United States Patent [19]

Redman

[11] 4,091,481

[45] May 30, 1978

[54] TOOTH PILLOW

[76] Inventor: Hallie G. Redman, 206 Aspen La., Highland Park, Ill. 60035

[21] Appl. No.: 794,980

[22] Filed: May 9, 1977

[51] Int. Cl.² .............................................. A47G 9/00
[52] U.S. Cl. .......................................... 5/337; 5/341
[58] Field of Search ............. 5/337, 338, 341; D6/94; D9/191; D19/59, 6; D34/55 S; D87/3 C

[56] References Cited

U.S. PATENT DOCUMENTS

| | | | |
|---|---|---|---|
| D. 232,213 | 7/1974 | Dobyns | D6/94 |
| D. 232,224 | 7/1974 | Dobyns | D6/94 |
| 3,789,546 | 2/1974 | Morrison | 5/337 |

*Primary Examiner*—Casmir A. Nunberg
*Assistant Examiner*—Alex Grosz
*Attorney, Agent, or Firm*—Gerald S. Geren

[57] ABSTRACT

Disclosed herein is a pillow shaped in a three-dimensional, tooth-like configuration. This tooth-shaped pillow comprises a top occlusel surface, an upper crown surface and at least one lower root-like projection. Secured to the crown surface is a tooth-and-coin receiving pocket in which the "tooth fairy" may deposit coins and other valuables in exchange for baby teeth which a child places therein.

1 Claim, 3 Drawing Figures

TOOTH PILLOW

FIELD OF THE INVENTION

This invention relates to a novelty device of particular interest to children of tooth losing age, and more particularly, to a tooth pillow novelty device for receiving and holding baby teeth and coins.

BACKGROUND OF THE INVENTION

Combinations of pillows having pockets secured to their exterior surfaces for the purpose of holding doll-like toys are shown by prior art devices, such as U.S. Pat. Nos. 1,651,738 and 3,789,546. However, applicant's invention differs structurally and functionally from such prior art devices as explained below.

Children, over 5 years old, begin to experience a maturation phenomena wherein nature replaces their temporary or "baby" teeth with permanent ones. The loss of a tooth and the cutting of its replacement is a painful and traumatic experience for young children and, of course, their parents share in the pain and trauma.

To reduce such anxiety, "tooth fairy" was invented and as the myth is told, if a child who loses one of his baby teeth places that tooth under his pillow, the tooth fairy will appear while he is asleep to replace the tooth with coins or other valuables.

Because children toss and turn in their sleep, coins placed beneath their pillows can easily fall to the floor. The result is a search by the child who has awakened to find his tooth gone and no reward in its place. Furthermore, it is desirable to provide a novelty item for use at the time of the tooth loss.

It is therefore an object of this invention to provide a tooth pillow novelty device of particular interest to children of tooth-losing age and which minimizes the problems of coin loss.

These and other objects will become apparent from the following description and appended claims.

BRIEF SUMMARY OF THE INVENTION

A three-dimensional, tooth-shaped pillow for receiving and holding valuables which includes an upper crown portion, a top occlusel biting surface and lower root-like projections. The occlusel surface is defined by a series of peripheral cusps forming a fossa therebetween. Secured to the crown portion, between the fossa and root-like projections, is a pocket having an upper tooth and coin receiving opening. The pillow is provided for use by young children and their parents who are desirous of exchanging baby teeth for money or other valuables.

DETAILED DESCRIPTION OF THE INVENTION

Figure 1:
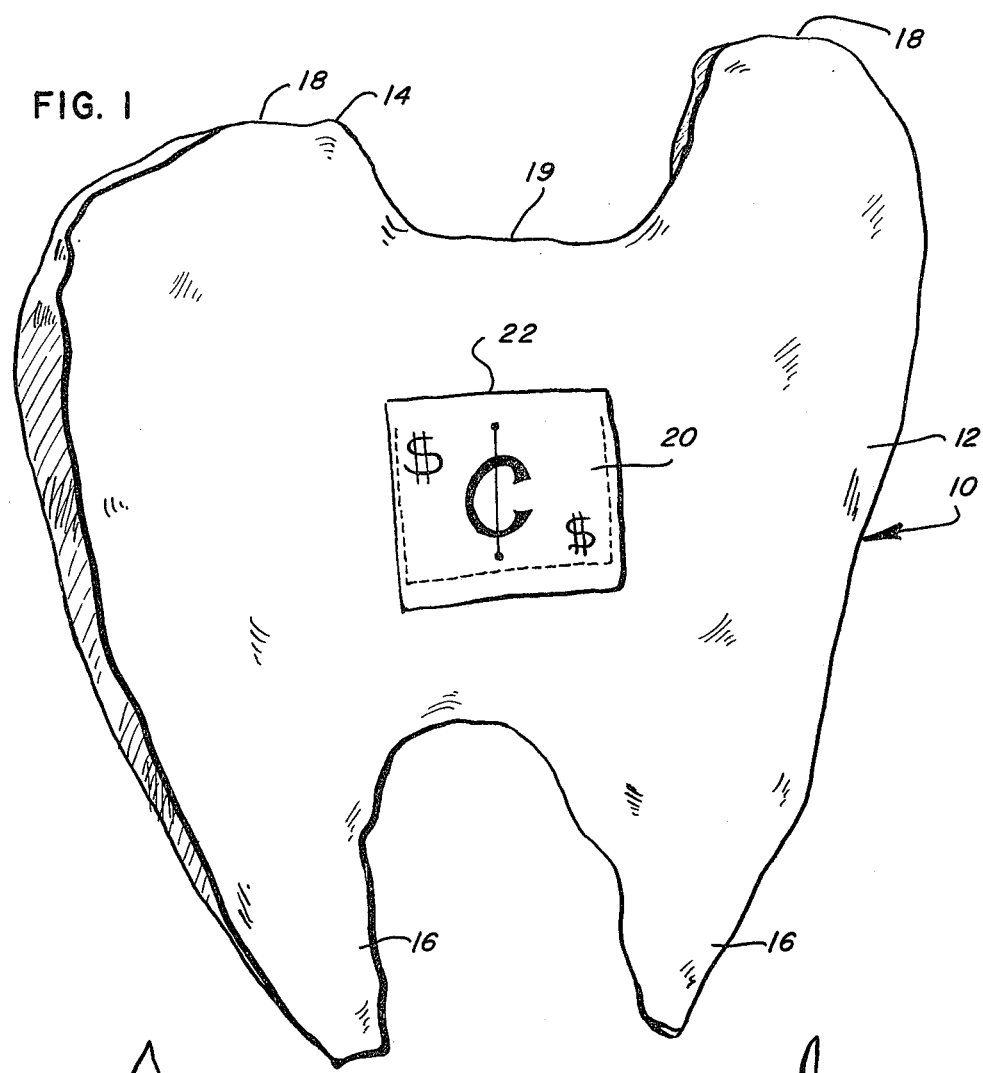
FIG. 1 is a perspective view of the tooth pillow of this invention and showing the tooth and coin receiving pocket attached to the crown portion.

The tooth pillow of this invention is illustrated generally as 10 in the drawings. It can be formed of any well-known filler material, such as foam, feathers, etc. An outer cover of linen or other soft fabric encapsulates the inner material to outline a three-dimensional sleeping pillow.

The encapsulating cover is shaped to form a large, simulated tooth. The tooth pillow 10 so formed includes an upper crown portion 12, a top occlusel biting portion 14 and downwardly extending root projections 16. The occlusel biting surface is formed by a series of raised cusp members 18 defining a recess or fossa 19 therebetween.

Figure 2:
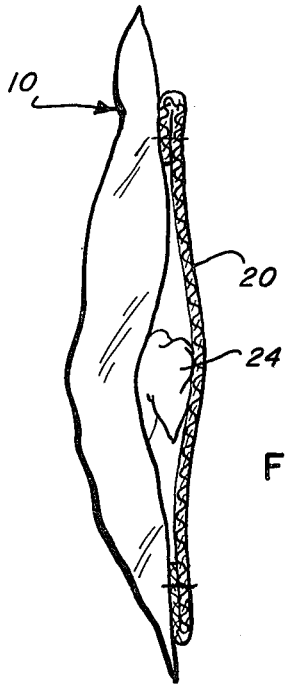
FIG. 2 is a top plan view of the tooth pillow of FIG. 1 and showing a tooth in the tooth and coin receiving pocket.
Figure 3:
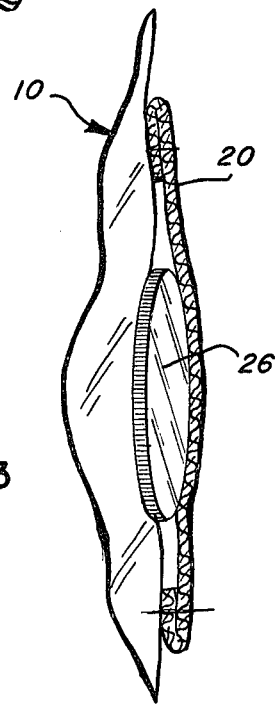
FIG. 3 is a top plan view of the tooth pillow of FIG. 1 and showing a coin in the tooth and coin receiving pocket.

A pocket 20 is secured, by sewing or other suitable means, to the upper crown portion 12 below the fossa 18 and above the root portion 16. The pocket 20 has an upper opening 22 for receiving teeth and coins. FIG. 2 clearly shows the pocket 20 snugly holding a tooth 24 therein, while FIG. 3 clearly depicts the same pocket snugly holding a coin 26 therein. As shown in FIG. 1, the pocket 20 may include decorative tooth-loss related indicia such as dollars and cents signs.

Before retiring for the evening, a child, who has recently lost a baby tooth, places that tooth in the opening 22 of the pocket 20. After he falls asleep, the "tooth fairy" is able to replace the tooth with coins or other valuables. Upon awakening the next morning, the child finds the valuables safely resting in the pocket of his tooth pillow.

While one form of the invention has been described, it will be understood that the invention may be utilized in other forms and environments, so that the purpose of the appended claims is to cover all such forms of devices not disclosed but which embody the invention disclosed herein.

It will be appreciated that numerous changes and modifications can be made to the embodiment shown herein without departing from the spirit and scope of this invention.

What is claimed and desired to be secured by Letters Patent of the United States is:

1. A tooth pillow novelty device for receiving tooth and coins comprising: filler material; an outer cover means shaped to form a three-dimensional pillow and encapsulating the filler material; and pocket means secured to the outer pillow surface, the improvement comprising in combination:

the pillow being tooth-shaped and including an upper crown portion and at least one lower root projection;

the crown portion having raised cusp members about the upper surface thereof, the cusp members forming a top occlusel biting surface, a fossa formed between the cusp members and the occlusel surface;

the pocket means being secured to the upper crown portion below the fossa and above at least one root projection, the pocket having an upper tooth and coin receiving opening;

at least part of the outer tooth pillow surface is covered with tooth-loss related indicia;

whereby the "tooth fairy" may replace children's baby teeth situated in the pocket with coins or other valuable commodities.

* * * * *